United States Patent [19]

Nagase et al.

[11] Patent Number: 5,616,317

[45] Date of Patent: Apr. 1, 1997

[54] POLYCATIONIC POLYMER AND POLYCATIONIC MICROBICIDAL AND ALGAECIDAL AGENT

[75] Inventors: Yu Nagase, Sagamihara; Takao Aoyagi, Nagareyama; Tomoko Akimoto, Zama; Kazunori Tanaka, Shizuoka; Kouichi Iwabuchi, Shizuoka; Yoshihiro Konagai, Shizuoka, all of Japan

[73] Assignees: Sagami Chemical Research Center, Tokyo; K·I Chemical Industry Co., Ltd., Shizuoka, both of Japan

[21] Appl. No.: 454,152

[22] PCT Filed: Dec. 21, 1993

[86] PCT No.: PCT/JP93/01847

§ 371 Date: Jun. 14, 1995

§ 102(e) Date: Jun. 14, 1995

[87] PCT Pub. No.: WO94/14872

PCT Pub. Date: Jul. 7, 1994

[30] Foreign Application Priority Data

Dec. 22, 1995 [JP] Japan ..................... 4-356485
Dec. 22, 1995 [JP] Japan ..................... 4-356486

[51] Int. Cl.$^6$ ............... C08G 73/00; A01N 33/12; A01N 43/40; A01N 55/00
[52] U.S. Cl. ............... 424/78.3; 424/78.36; 514/332; 514/334; 504/155; 422/6; 422/16; 427/332
[58] Field of Search ................ 427/332; 422/6, 422/16; 504/155; 514/332, 334; 424/78.3, 78.36

[56] References Cited

U.S. PATENT DOCUMENTS 2,261,002  10/1941  Ritter ..................... 260/570
2,271,378  1/1942  Searle ..................... 167/22

FOREIGN PATENT DOCUMENTS

| 0319156 | 6/1989 | European Pat. Off. . |
| 49-18146 | 2/1974 | Japan . |
| 52-155528 | 12/1977 | Japan . |
| 53-25700 | 3/1978 | Japan . |
| 57-15306 | 1/1982 | Japan . |

*Primary Examiner*—Frederick Krass
*Attorney, Agent, or Firm*—Oblon, Spivak, McClelland, Maier & Neustadt, P.C.

[57] ABSTRACT

A polycationic microbicidal and algaecidal agent containing as an active ingredient a polymer comprising repeating units represented by the formula (I) and having a number average molecular weight of at least 1,000, and a microbicidal and algaecidal method using the polymer:

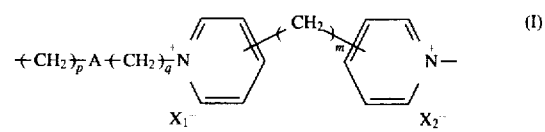

(wherein A is a single bond, an oxygen atom, a phenylene group, a dioxyethylene group or a tetramethyldisiloxane group, $X_1^-$ and $X_2^-$ may be the same or different and are counter anions in quaternary salts, p and q may be the same or different and are integers of from 1 to 6, and m is an integer of from 1 to 6, provided that A, $X_1^-$, $X_2^-$, p, q and m may be the same or optionally different for every repeating unit).

6 Claims, No Drawings

POLYCATIONIC POLYMER AND POLYCATIONIC MICROBICIDAL AND ALGAECIDAL AGENT

TECHNICAL FIELD

The present invention relates to a polycationic polymer having pyridinium groups in its main chain structure, and a microbicidal and algaecidal agent containing this polymer as an active ingredient and a microbicidal and algaecidal method using this polymer.

BACKGROUND ART

Heretofore, quaternary ammonium salts have been used for various applications as cationic surfactants. Some of them are known to have strong microbicidal activities. Among them, an alkyldimethylbenzyl ammonium chloride (benzalconium chloride) is utilized in a wide range of fields by virtue of its excellent microbicidal effects (the carbon chain length of the alkyl group is mainly from $C_{12}$ to $C_{14}$).

On the other hand, developments have been carried out for polymer compounds having microbicidal activities. In particular, an attempt has been made to produce a high molecular weight product by e.g. polymerization of a monomer having a substituent containing a quaternary nitrogen such as an ammonium salt or a pyridinium salt. Specific examples include an acrylic polymer having quaternary ammonium groups as ester residues (Japanese Unexamined Patent Publication No. 6394/1978), a polystyrene derivative having quaternary ammonium groups as substituents on benzene rings (Japanese Unexamined Patent Publication No. 246205/1986), a polyvinylpyridine derivative having pendant pyridinium groups (Japanese Unexamined Patent Publication No. 310803/1988) and a polymer having benzyl ammonium or benzyl pyridinium groups in its side chains (Japanese Unexamined Patent Publication No. 26610/1989).

However, the above-mentioned low molecular weight type quaternary ammonium salts are limited in their applications for reasons such that they have foaming properties in their aqueous solution systems, they are inferior in the thermal stability, or their absorptivity to various material components is remarkable, or the effective ingredients are likely to be discharged outside or tend to separate or sediment inside so that the microbicidal and algaecidal activities deteriorate. Further, conventional polymer-type microbicides containing quaternary nitrogen in their side chains have had a problem such that the activities deteriorate as compared with low molecular weight compounds or totally extinct, so that the microbicidal activities are not necessarily adequate.

DISCLOSURE OF THE INVENTION

The present inventors have made strenuous efforts in study to present a polycationic microbicidal and algaecidal agent which provides adequate activities when used as a microbicidal and algaecidal agent and is thermally stable without a foaming property and which is useful for a wide range, and a novel microbicidal and algaecidal method. As a result, they have found that a polycationic polymer having pyridinium groups in the main chain structure, which is obtainable by the reaction of a specific dipyridine compound and a dihalogen compound, has excellent microbicidal activities as well as algaecidal and microbicidal activities against algae and a wide range of other hazardous microorganisms. The present invention has been accomplished on the basis of this discovery.

Namely, the present invention provides a polycationic polymer comprising repeating units of the following formula (I):

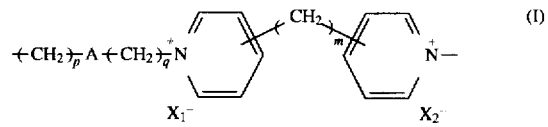

(wherein A is a single bond, an oxygen atom, a phenylene group, a dioxyethylene group or a tetramethyldisiloxane group, $X_1^-$ and $X_2^-$ may be the same or different and are counter anions in quaternary salts, p and q may be the same or different and are integers of from 1 to 6, and m is an integer of from 1 to 6, provided that A, $X_1^-$, $X_2^-$, p, q and m may be the same or optionally different for every repeating unit) and having a number average molecular weight of at least 1,000.

Further, the present invention provides a polycationic microbicidal and algaecidal agent containing, as an active ingredient, a polymer comprising repeating units of the following formula (I):

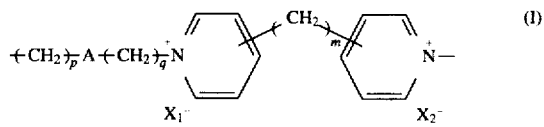

(wherein A is a single bond, an oxygen atom, a phenylene group, a dioxyethylene group or a tetramethyldisiloxane group, $X_1^-$ and $X_2^-$ may be the same or different and are counter anions in quaternary salts, p and q may be the same or different and are integers of from 1 to 6, and m is an integer of from 1 to 6, provided that A, $X_1^-$, $X_2^-$, p, q and m may be the same or optionally different for every repeating unit) and having a number average molecular weight of at least 1,000, and a microbicidal and algaecidal method characterized by the use of said polymer.

As the counter anions in quaternary salts represented by $X_1^-$ and $X_2^-$ in the above formula (I), halogen ions such as $F^-$, $Cl^-$, $Br^-$ or $I^-$, conjugate bases of mineral acids, such as hydroxyl ions, carbonate ions, sulfate ions, hydrogen sulfate ions, sulfite ions, nitrate ions or phosphate ions, or conjugate bases of organic acids, such as carboxylate ions, sulfonate ions or phosphate ions, may, for example, be mentioned.

The polymer comprising repeating units of the above formula (I) according to the present invention, can be produced, for example, by the following method. Namely, among polymers comprising repeating units of the above formula (I), the one wherein $X_1^-$ and $X_2^-$ are halogen ions, can easily be produced in good yield by reacting a dipyridine compound of the following formula (II):

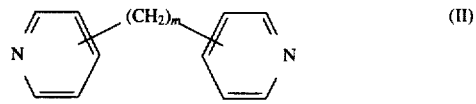

(wherein m is an integer of from 0 to 6) and a dihalogen compound of the following formula (III):

$$Y + CH_2 \underset{p}{\rightarrow} A + CH_2 \underset{q}{\rightarrow} Y \qquad (III)$$

(wherein A is a single bond, an oxygen atom, a phenylene group, a dioxyethylene group or a tetramethyldisiloxane group, Y is a halogen atom, and p and q may be the same or different and are integers of from 1 to 6). Further, those wherein $X_1^-$ and $X_2^-$ are other than halogen ions, can be easily obtained by ion exchanging the halogen ions as the counter anions of the polymer comprising repeating units of the above formula (I) thus obtained to the corresponding conjugate bases of mineral acids or organic acids.

This reaction is preferably conducted in a solvent, and the solvent to be used may be any solvent so long as it is capable of dissolving the respective starting materials and the obtained polymer. For example, water, methanol, ethanol, propanol, isopropanol, ethylene glycol, acetone, acetonitrile, dimethylformamide, dimethylacetamide, dimethylsulfoxide and solvent mixtures thereof may be suitably employed. This reaction proceeds smoothly usually within a temperature range of from room temperature to about 150° C.

The dipyridine compound of the above formula (II) to be used in the above reaction, may, for example, be 4,4'-dipyridyl, 2,2'-dipyridyl, di(4-pyridyl)methane, di(2-pyridyl)methane, 1,2-di(4-pyridyl)ethane, 1,2-di(2-pyridyl)ethane, 1,3-di(4-pyridyl)propane, 1,3-di(2-pyridyl)propane, 1,4-di(4-pyridyl)butane, 1,5-di(4-pyridyl)pentane, or 1,6-di(4-pyridyl)hexane. However, from the viewpoint of e.g. the price, the reactivity and the usefulness of the product, 4,4'-dipyridyl and 1,3-di(4-pyridyl)propane are preferred.

The dihalogen compound of the above formula (III) may, for example, be 1,2-dichloroethane, 1,2-dibromoethane, 1,2-diiodoethane, 1,3-dichloropropane, 1,3-dibromopropane, 1,3-diiodopropane, 1,4-dichlorobutane, 1,4-dibromobutane, 1,4-diiodobutane, 1,5-dichloropentane, 1,5-dibromopentane, 1,5-diiodopentane, 1,6-dichlorohexane, 1,6-dibromohexane, 1,6-diiodohexane, 1,7-dichloroheptane, 1,7-dibromoheptane, 1,7-diiodoheptane, 1,8-dichlorooctane, 1,8-dibromooctane, 1,8-diiodooctane, 1,2-di(2-chloroethyl)ether, 1,2-di(2-bromoethyl)ether, 1,2-di(2-iodoethyl)ether, 1,2-di(2-chloroethoxy)ethane, 1,2-di(2-bromoethoxy)ethane, 1,2-di(2-iodoethoxy)ethane, p-di(chloromethyl)benzene, p-di(bromomethyl)benzene, p-di(iodomethyl)benzene, m-di(chloromethyl)benzene, m-di(bromomethyl)benzene, m-di(iodomethyl)benzene, o-di(chloromethyl)benzene, o-di(bromomethyl)benzene, o-di(iodomethyl)benzene, 1,3-di(3-chloropropyl)-1,1,3,3-tetramethyldisiloxane, 1,3-di(3-bromopropyl)-1,1,3,3-tetramethyldisiloxane, 1,3-di(3-iodopropyl)-1,1,3,3-tetramethyldisiloxane, 1,3-di(4-chlorobutyl)-1,1,3,3-tetramethyldisiloxane, 1,3-di(4-bromobutyl)-1,1,3,3-tetramethyldisiloxane, 1,3-di(4-iodobutyl)-1,1,3,3-tetramethyldisiloxane, 1,3-di(5-chloropentyl)-1,1,3,3-tetramethyldisiloxane, 1,3-di(5-bromopentyl)-1,1,3,3-tetramethyldisiloxane, 1,3-di(5-iodopentyl)-1,1,3,3-tetramethyldisiloxane, 1,3-di(6-chlorohexyl)-1,1,3,3-tetramethyldisiloxane, 1,3-di(6-bromohexyl)-1,1,3,3-tetramethyldisiloxane, or 1,3-di(6-iodohexyl)-1,1,3,3-tetramethyldisiloxane.

The number average molecular weight of the polymer comprising repeating units of the above formula (I) according to the present invention, is at least 1,000, more preferably at least 3,000. With the one having a lower molecular weight, the microbicidal and algaecidal effects are low. The molecular weight is measured by a conventional method such as gel permeation chromatography, an osmotic pressure method, a light-scattering method or a viscosity method.

The polymer comprising repeating units of the above formula (I) according to the present invention has a large content of pyridinium groups, and thus it has high water-solubility and is suitable for use as a microbicidal and algaecidal agent. The solvent to be used for dissolving this polymer, is properly selected taking the solubility into consideration. However, water and an alcohol solvent such as methanol, ethanol or ethylene glycol are suitable and may be used alone or in combination.

The polycationic microbicidal and algaecidal agent of the present invention is the one containing, as an active ingredient, the polymer comprising repeating units of the above formula (I), and various formulations are conceivable. For example, the above polymer may be dissolved or dispersed in water or an aqueous inorganic salt solution to use as a solution, or may be supported on a suitable carrier. Otherwise, the above polymer may be formed into a polymer film, or may be used as it is, as a solid formulation. Further, a liquid formulation containing the above polymer may be coated or impregnated to a molded product of e.g. fiber, glass or plastic to impart it microbicidal and algaecidal activities. Otherwise, the above polymer may be incorporated into cleaning agents such as soaps or shampoos. And, if necessary, it can be used in combination as a mixture with a conventional agent of a quaternary ammonium salt such as an alkyldimethylbenzyl ammonium chloride (benzalconium chloride), didecyldimethyl ammonium chloride or polyhexamethylene biguanidine hydrochloride, or as a mixture with a common industrial microbicide, for example, a propionamide (such as 2,2-dibromo-3-nitrilopropionamide), a nitroalcohol derivative (such as 2-bromo-2-nitropropane-1, 3-diol or 2,2-dibromo-2-nitroethanol), an isothiazoline (such as 1,2-benzisothiazolin-3-one or 5-chloro-2-methyl-4-isothiazolin-3-one), an alkylene bisthiocyanate (such as methylene-bisthiocyanate or ethylenebisthiocyanate) or a halogenated acetate derivative (such as 1,4-bis(bromoacetoxy)ethane or 1,4-bis(bromoacetoxy)-2-butene), or may be used in situ in admixture with or in an alternative fashion with these agents, without impairing the properties of the polycationic microbicidal and algaecidal agent of the present invention.

The polycationic microbicidal and algaecidal agent of the present invention can be used for the skin, hair, clothings, tablewares, medical equipments or for sterilization or disinfection of the environment such as the floor of a food plant, or for sterilization or cleaning of a process. Further, it is useful for controlling microbe and algae for water treatment for e.g. pools or cooling water, for slime control, or as a disinfecting deodorant for public facilities such as trains, hotels or meeting places, or animal cages. The microbicidal and algaecidal method using the above polymer of the present invention, can be accomplished by adding this polymer to the above systems to be microbicidally or algaecidally treated. At the time of the addition, the polymer may be used in various formulations as described above.

BEST MODE FOR CARRYING OUT THE INVENTION

Now, the present invention will be described in further detail with reference to Examples and Test Examples. However, the present invention is by no means restricted by such examples.

EXAMPLE 1

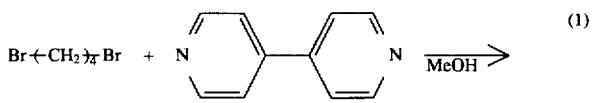

(1)

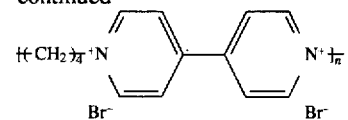

5.93 g (27.8 mmol) of 1,4-dibromobutane and 4.34 g (27.8 mmol) of 4,4-dipyridyl were dissolved in 50 ml of methanol. This solution was refluxed at about 80° C. for 15 hours. Then, this reaction solution was poured into excess ethyl ether. Obtained precipitate was recovered and then again dissolved in. methanol, and reprecipitation in excess ethyl ether was repeated, whereby 7.69 g of a polymer of the above formula (1) was obtained as a yellow solid. The number average molecular weight of the obtained polymer was measured by gel permeation chromatography, whereby it was 9,500 as calculated as polyethylene glycol.

$^1$H-NMR, δ (D$_2$O, ppm); 1.86–2.66 (m, 4H), 3.58 (m, 4H), 8.57 (m, 4H), 9.13 (m, 4H).

IR (KBr, cm$^{-1}$); 3433, 3038, 2924 1640, 1560, 1508, 1450, 1180, 814.

EXAMPLE 2

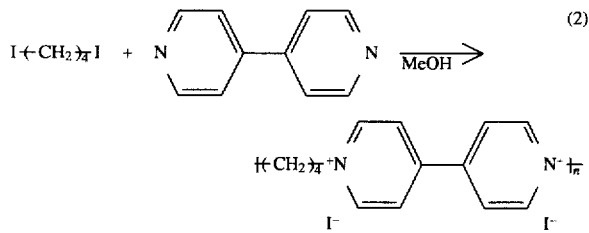

6.94 g (22.6 mmol) of 1,4-diiodobutane and 3.58 g (22.6 mmol) of 4,4'-dipyridyl were dissolved in 50 ml of methanol. This solution was refluxed at about 80° C. for hours. Then, this reaction solution was poured into excess ethyl ether. Obtained precipitate was recovered and then dissolved again in methanol, and reprecipitation in excess ethyl ether was repeated, whereby 7.30 g of a polymer of the above formula (2) was obtained as a red solid. The number average molecular weight of the obtained polymer was measured by gel permeation chromatography, whereby it was 15,000 as calculated as polyethylene glycol.

$^1$H-NMR, δ (D$_2$O, ppm); 2.24 (m, 4H), 3.44 (m,4H), 8.56 (m, 4H), 9.11 (m, 4H).

IR (KBr, cm$^{-1}$); 3445, 3026, 2928, 1640, 1560, 1508, 1449, 1179, 817.

EXAMPLE 3

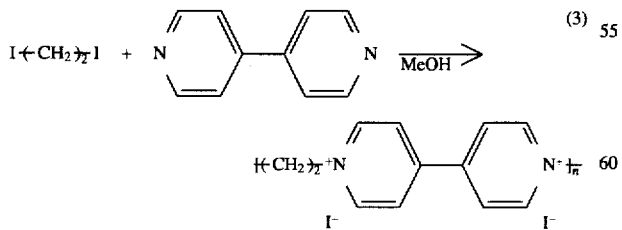

7.00 g (24.8 mmol) of 1,2-diiodoethane and 3.88 g (24.8 mmol) of 4,4'-dipyridyl were dissolved in 50 ml of methanol. This solution was refluxed at about 80° C. for 15 hours. Then, this reaction solution was poured into excess ethyl ether. Obtained precipitate was recovered, and then dissolved again in methanol, and reprecipitation in excess ethyl ether was repeated, whereby 3.93 g of a polymer of the above formula (3) was obtained as a brown solid. The number average molecular weight of the obtained polymer was measured by gel permeation chromatography, whereby it was 8,000 as calculated as polyethylene glycol.

$^1$H-NMR, δ (D$_2$O, ppm); 3.43 (s, 4H), 7.87 (m, 4H), 8.79 (m, 4H).

IR (KBr, cm$^{-1}$); 3440, 3025, 2930, 1640, 1560, 1510, 1450, 1179, 815.

EXAMPLE 4

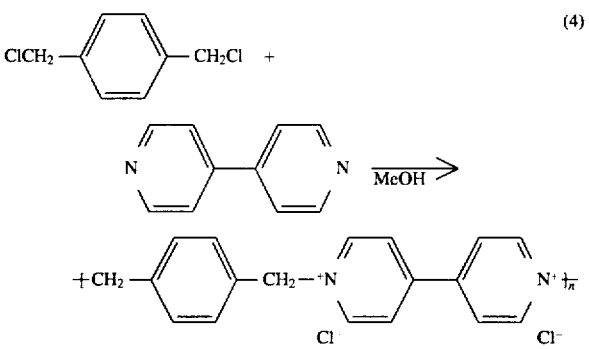

6.00 g (34.4 mmol) of p-di(chloromethyl)benzene and 5.35 g (34.3 mmol) of 4,4'-dipyridyl were dissolved in 50 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 8.41 g of a polymer of the above formula (4) was obtained as a white solid. The number average molecular weight of the obtained polymer was measured by gel permeation chromatography, whereby it was 7,500 as calculated as polyethylene glycol.

$^1$H-NMR, δ (D$_2$O, ppm); 6.07 (s, 4H), 7.71 (s, 4H), 8.63 (d, 4H, J=2.0 Hz), 9.24 (d, 4H, J=2.0 Hz).

IR (KBr, cm$^{-1}$); 3422, 3040, 2930, 1636, 1560, 1502, 1447, 1161, 795.

EXAMPLE 5

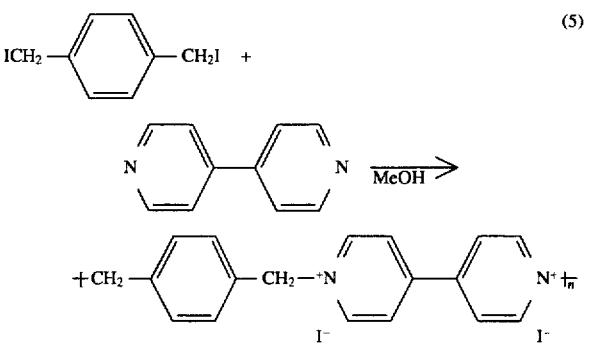

1.70 g (4.79 mmol) of p-di(iodomethyl)benzene and 0.74 g (4.79 mmol) of 4,4'-dipyridyl were dissolved in 50 ml of acetone. This solution was refluxed at about 80° C. for 15 hours. Then, this reaction solution was concentrated and dissolved in dimethylsulfoxide. The solution was poured into excess ethyl ether. Obtained precipitate was recovered and then again dissolved in dimethylsulfoxide, and reprecipitation in excess ethyl ether was repeated, whereby 2.24 g of a polymer of the above formula (5) was obtained as a dark red solid. The number average molecular weight of the obtained polymer was measured by gel permeation chromatography, whereby it was 74,000 as calculated as polyethylene glycol.

$^1$H-NMR δ (DMSO-$d_6$, ppm); 6.72 (s, 4H), 8.47 (s, 4H), 9.41 (d, 4H), 10.06 (d, 4H).

IR (KBr, cm$^{-1}$); 3445, 3025, 2915, 1640, 1558, 1510, 1450, 1162, 800.

EXAMPLE 6

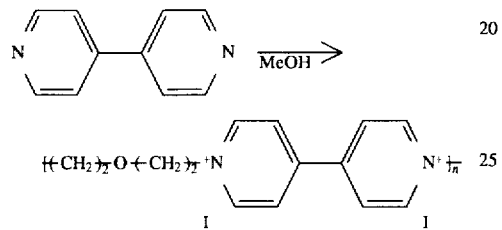

7.00 g (21.5 mmol) of di(2-iodoethyl)ether and 3.36 g (21.5 mmol) of 4,4'-dipyridyl were dissolved in 50 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 4.23 g of a polymer of the above formula (6) was obtained as a blackish brown solid. The number average molecular weight of the obtained polymer was measured by gel permeation chromatography, whereby it was 33,000 as calculated as polyethylene glycol.

$^1$H-NMR δ (DMSO-$d_6$, ppm); 4.34 (m, 4H), 5.20 (m, 4H), 9.16 (m, 4H), 9.61 (m, 4H).

IR (KBr, cm$^{-1}$); 3450, 3050, 1640, 1555, 1442, 1218, 1180, 810.

EXAMPLE 7

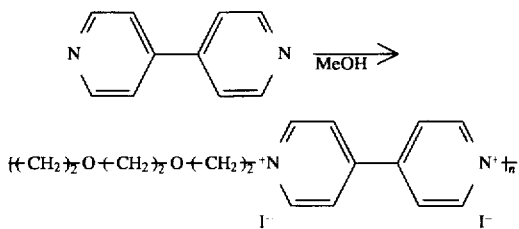

7.00 g (18.9 mmol) of 1,2-di(2-iodoethoxy)ethane and 2.96 g (18.9 mmol) of 4,4'-dipyridyl were dissolved in 50 ml of methanol. This solution was refluxed at about 80° C. for 15 hours. Then, this reaction solution was poured into excess ethyl ether. Obtained precipitate was recovered, and then dissolved again in methanol, and reprecipitation in excess ethyl ether was repeated, whereby 4.08 g of a polymer of the above formula (7) was obtained as a brown solid. The number average molecular weight of the obtained polymer was measured by gel permeation chromatography, whereby it was 16,000 as calculated as polyethylene glycol.

$^1$H-NMR δ ($D_2O$, ppm); 3.76 (m, 4H), 4.18 (m, 4H), 4.96 (m, 4H), 8.53 (m, 4H), 9.10 (m, 4H).

IR (KBr, cm$^{-1}$); 3448, 3045, 1640, 1550, 1435, 1218, 1175, 800.

EXAMPLE 8

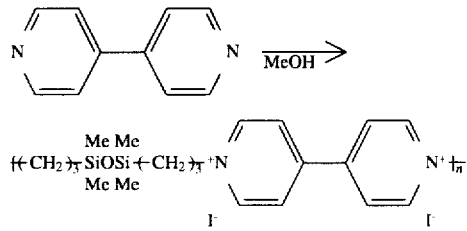

3.00 g (6.38 mmol) of 1,3-di(3-iodopropyl)-1,1,3,3-tetramethyldisiloxane and 1.00 g (6.38 mmol) of 4,4'-dipyridyl were dissolved in 10 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 3.00 g of a polymer of the above formula (8) was obtained as an orange colored solid. The number average molecular weight of the obtained polymer was measured by gel permeation chromatography, whereby it was 7,300 as calculated as polyethylene glycol.

$^1$H-NMR δ (DMSO-$d_6$, ppm); 0.05 (s, 12H), 0.43 (m, 4H), 1.92 (m, 4H), 4.59 (m, 4H), 8.69 (m, 4H), 9.26 (m, 4H).

IR (KBr, cm$^{-1}$); 3460, 3050, 2960, 1640, 1560, 1445, 1255, 1185, 1060, 820, 800.

EXAMPLE 9

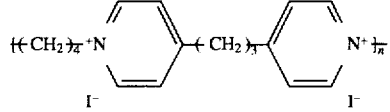

6.94 g (22.6 mmol) of 1,4-diiodobutane and 4.48 g (22.6 mmol) of 1,3-di(4-pyridyl)propane were dissolved in 50 ml of methanol. This solution was refluxed at about 80° C. for 15 hours. Then, this reaction solution was concentrated and then dissolved in dimethylformamide. The solution was poured into excess ethyl ether. Obtained precipitate was recovered and dissolved again in dimethylformamide, and reprecipitation in excess ethyl ether was repeated, whereby 4.50 g of a polymer of the above formula (9) was obtained as a black solid. The number average molecular weight of the obtained polymer was measured by gel permeation chromatography, whereby it was 64,000 as calculated as polyethylene glycol.

$^1$H-NMR δ (D$_2$O+DMSO-d$_6$, ppm); 1.63 (m, 6H), 2.53 (m, 4H), 4.11 (m, 4H), 7.52 (d, 4H, J=0.36 Hz ), 8.35 (d, 4H, J=0.36 Hz).

IR (KBr, cm$^{-1}$); 3450, 3030, 2920, 1640, 1555, 1450, 1175, 820.

EXAMPLE 10

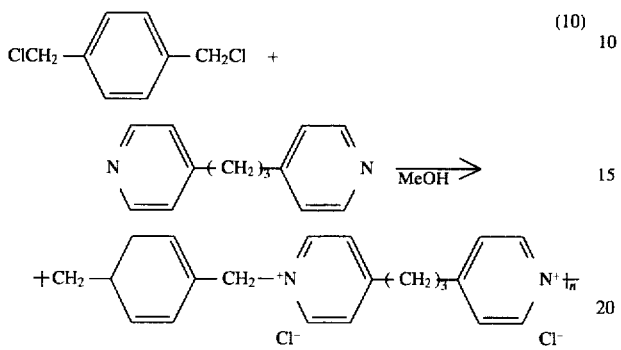

5.00 g (28.6 mmol) of p-di(chloromethyl)benzene and 5.66 g (28.6 mmol) of 1,3-di(4-pyridyl)propane were dissolved in 50 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 4.50 g of a polymer of the above formula (10) was obtained as a milky white solid. The number average molecular weight of the obtained polymer was measured by gel permeation chromatography, whereby it was 40,000 as calculated as polyethylene glycol.

$^1$H-NMR δ (CD$_3$OD, ppm); 1.71 (m, 2H), 2.59 (t, 4H, J=0.48 Hz), 5.38 (S, 4H), 7.14 (s, 4H), 8.07 (d, 4H, J=0.48 Hz), 8.98 (d, 4H, J=0.48 Hz)

IR (KBr, cm$^{-1}$); 3423, 3040, 1637, 1510, 1470, 1155, 829, 758.

EXAMPLE 11

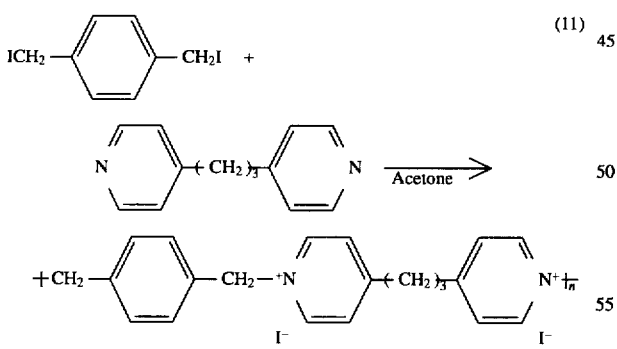

0.24 g (0.67 mmol) of p-di(iodomethyl)benzene and 0.13 g (0.67 mmol) of 1,3-di(4-pyridyl)propane were dissolved in 10 ml of acetone. This solution was refluxed at about 80° C. for 15 hours. Then, this reaction solution was concentrated and then dissolved in dimethylsulfoxide. The solution was poured into excess ethyl ether. Obtained precipitate was recovered and then dissolved again in dimethylsulfoxide, and reprecipitation in excess ethyl ether was repeated, whereby 0.32 g of a polymer of the above formula (11) was obtained as a yellowish brown solid. The number average molecular weight of the obtained polymer was measured by gel permeation chromatography, whereby it was 60,000 as calculated as polyethylene glycol.

$^1$H-NMR δ (DMSO-d$_6$+D$_2$O, ppm); 2.00 (m, 2H), 2.93 (m, 4H), 5.72 (m, 4H), 7.55 (s, 4H), 8.03 (m, 4H), 8.97 (m, 4H).

IR (KBr, cm$^{-1}$); 3450, 3050, 1638, 1510, 1440, 1152, 802.

EXAMPLE 12

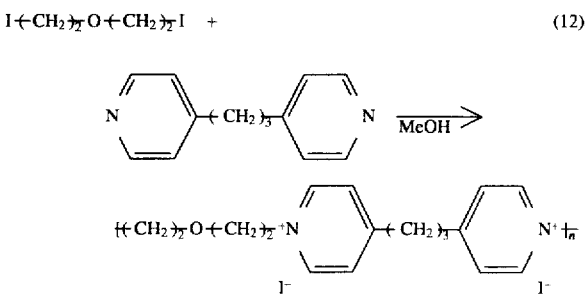

4.00 g (12.3 mmol) of di(2-iodoethyl)ether and 2.43 g (12.3 mmol) of 1,3-di(4-pyridyl)propane were dissolved in 40 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 4.50 g of a polymer of the above formula (12) was obtained as a yellowish green solid. The number average molecular weight of the obtained polymer was measured by gel permeation chromatography, whereby it was 46,000 as calculated as polyethylene glycol.

$^1$H-NMR δ (D$_2$O, ppm); 2.10 (m, 2H), 3.13 (m, 4H), 4.10 (m, 4H), 4.82 (m, 4H), 8.06 (d, 4H, J=5.4 Hz), 8.75 (d, 4H, J=5.4 Hz)

IR (KBr, cm$^{-1}$); 3420, 3045, 1640, 1505, 1470, 1155, 829.

EXAMPLE 13

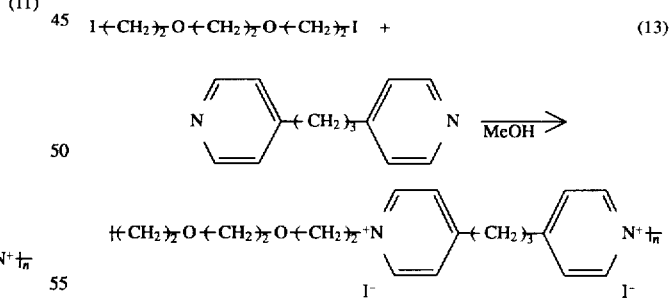

5.00 g (13.5 mmol) of 1,2-di(2-iodoethoxy)ethane and 2.68 g (13.5 mmol) of 1,3-di(4-pyridyl)propane were dissolved in 40 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 5.00 g of a polymer of the above formula (13) was obtained as a yellowish green solid. The number average molecular weight of the obtained polymer was measured by gel permeation chromatography, whereby it was 51,000 as calculated as polyethylene glycol.

$^1$H-NMR δ (D$_2$O, ppm); 2.20 (m, 2H), 3.10 (m, 4H), 3.66 (m, s, 4H), 4.03 (m, 4H), 4.77 (m, 4H), 8.01 (d, 4H, J=5.4 Hz), 8.73 (m, 4H, J=5.4 Hz).

IR (KBr, cm$^{-1}$); 3415, 3048, 1640, 1510, 1455, 1150, 829.

EXAMPLE 14

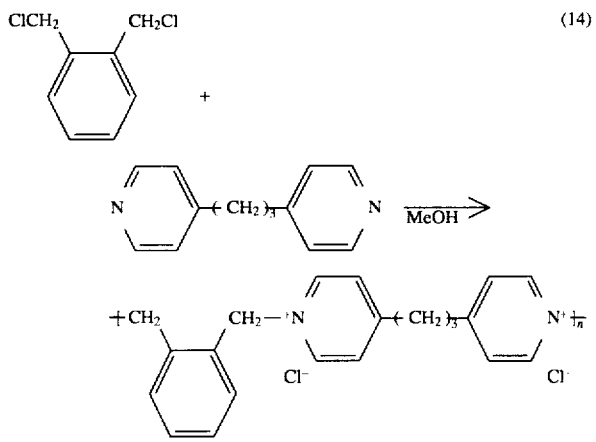

2.00 g (11.4 mmol) of o-di(chloromethyl)benzene and 2.26 g (11.4 mmol) of 1,3-di(4-pyridyl)propane were dissolved in 20 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 4.20 g of a polymer of the above formula (14) was obtained as a blue solid. The number average molecular weight of the obtained polymer was measured by gel permeation chromatography, whereby it was 23,000 as calculated as polyethylene glycol.

$^1$H-NMR δ (D$_2$O, ppm); 2.18 (m, 2H), 3.18 (m, 4H), 6.00 (m, s, 4H), 7.38 (m, 2H), 7.70 (m, 2H), 8.03 (m, 4H), 8.76 (m, 4H).

IR (KBr, cm$^{-1}$); 3420, 3050, 1635, 1510, 1465, 1150, 820, 755.

EXAMPLE 15

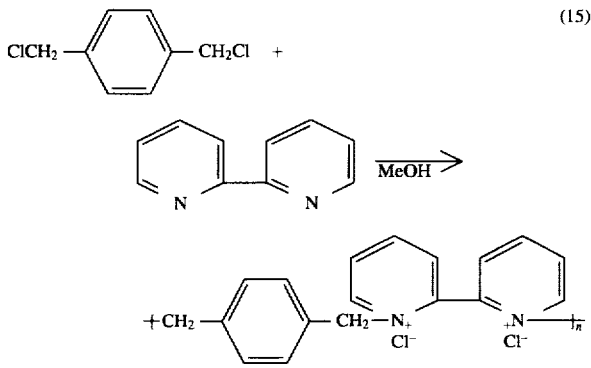

2.24 g (12.8 mmol) of p-di(chloromethyl)benzene and 2.00 g (12.8 mmol) of 2,2'-dipyridyl were dissolved in 50 ml of methanol. This solution was refluxed at about 80° C. for 15 hours. Then, this reaction solution was poured into excess ethyl ether. Obtained precipitate was recovered and then dissolved again in methanol, and reprecipitation in excess ethyl ether was repeated, whereby 1.50 g of a polymer of the above formula (15) was obtained as a red solid. The number average molecular weight of the obtained polymer was measured by gel permeation chromatography, whereby it was 2,200 as calculated as polyethylene glycol.

$^1$H-NMR δ (D$_2$O, ppm); 5.40 (d, 1H), 6.30 (m, 1H), 6.64 (m, 1H), 7.13 (m, 4H), 7.71 (m, 6H), 8.15 (d, 2H), 8.53 (m, 1H).

IR (KBr, cm$^{-1}$); 2930, 2480, 1940, 1710, 1615, 1580, 1505, 1440, 1310, 1200, 1080, 890, 760.

TEST EXAMPLE 1

(Confirmation of microbicidal activities against bacteria and fungi)

With respect to the polymers obtained in Examples 1 to 15 and comparative agents, a test of microbicidal activities was conducted. The types of strains used in the test, the method and the results are shown below.

(1) Test strains

Industrially important hazardous six types of bacteria and two types of fungi were selected, and a total of 8 strains as identified below were subjected to the test.

Bacteria
  Bs: *Bacillus subtilis*
  I.F.O 3007
  Ec: *Escherichia coli* N. I. H. J.
  Pa: *Pseudomonas aeruginosa*
  I. A. M. 1054
  Sa: *Staphylococcus aureus*
  A. T. C. C. 6538p
  Ss: *Shigella sonnei*
  St: *Salmonella typhimurium*
Fungi
  An: *Aspergillus niger*
  A. T. C. C. 6275
  Ps: *Penicillium steckii*
  I. A. M. 7048

(2) Test method

The polymers obtained in Examples 1 to 15 were accurately weighed and respectively adjusted to 200 μg/ml. This adjusted solution was diluted to concentrations of 200, 100, 50, 25, 10, 5, 2.5 and 1 μg/ml to obtain test solutions. Then, a test strain stored in a test tube was taken by a platinum loop and put into a test tube containing 10 ml of a normal bouillon culture medium (the one having 3 g of meat extract, 10 g of peptone and 5 g of sodium chloride dissolved in 1,000 ml of water), followed by incubation at 30° C. for 48 hours. Then, it was stored at 20° C. to obtain a culture solution of the test strain. 9 ml of the obtained test solution was put into a sterilized 10 ml L-letter test tube, and 1 ml of the culture solution of the above test strain was inoculated thereto to let the agent act thereon at 30° C. for 30 minutes. After the action, 1 ml of this solution was put into 100 ml of sterilized water to obtain a uniform diluted solution. Then, 1 ml of this diluted solution was sampled to obtain an action solution. The strains in such action solutions were further cultured, respectively, by the following methods, and the microbicidal activities by the respective polymers were evaluated. Bacteria: 10 μl of the action solution was taken into a sterilized Petri dish, and 5 ml of a culture medium for bacteria (Tryptic soy agar culture medium, manufactured by Nissui Seiyaku K.K.) was cast and solidified, followed by incubation at 30° C. for two days. Fungi: 5 ml of a culture medium for fungi (potato dextrose agar culture medium, manufactured by Nissui Seiyaku K.K.) was cast and solidified in a sterilized Petri dish, and then 10 µl of the action solution was added thereto, followed by incubation at 30° C. for 4 days.

Determination of the microbicidal activities was made by visually inspecting the colonies of the respective bacteria and fungi, whereby a case where the culture medium was clear and no colony was detected, was determined to be sterilized. Among test solutions in which strains were sterilized, the lowest concentration was taken as the minimum microbicidal concentration of that compound.

With respect to cases where the respective polymers obtained in Examples 1 to 15 were used, the minimum microbicidal concentrations of the respective bacteria and fungi are shown in Table 1. As is apparent from Table 1, these polymers all exhibited excellent microbicidal activities at very low concentrations.

Comparative Example 1

By the reactions shown below, compounds (16), (17) and (18) having chemical structures similar to repeating units of the polycationic polymer used in the present invention, were synthesized, respectively, and their microbicidal activities were evaluated in the same manner as in Test Example 1. The results are also shown in Table 1. The syntheses were carried out in the same manner as the method described in Example 1 using the starting compounds as identified in the following reaction formulas. As a result, the minimum microbicidal concentrations of these compounds were at least 100 µg/ml with every test strain, and they were found to have no substantial microbicidal effects.

Further, with respect to benzalconium chloride (19) which is widely used as an industrial microbicide, a test was carried out in the same manner. The results are also shown in Table 1.

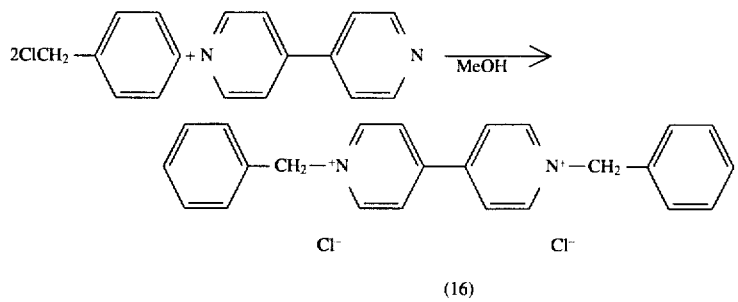

(16)

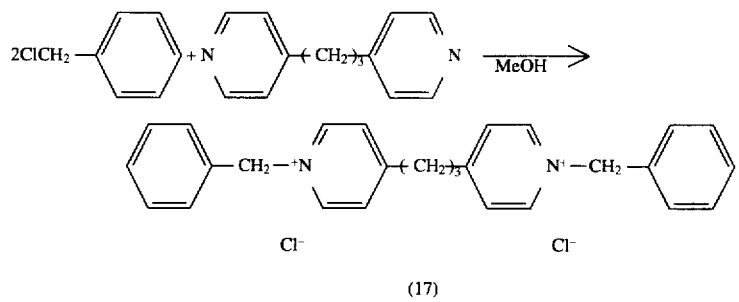

(17)

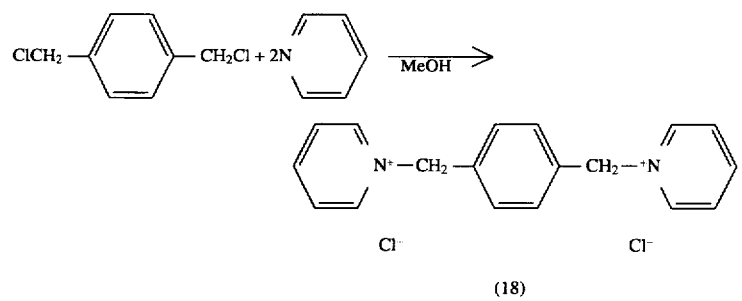

(18)

TABLE 1

| No. | Minumum microbicidal concentration (μg/ml) | | | | | | | |
|---|---|---|---|---|---|---|---|---|
| | Bs | Ec | Pa | Sa | An | Ps | Ss | St |
| Agent No. of Example | | | | | | | | |
| (1) | 5 | 2.5 | 5 | 2.5 | 5 | 5 | 5 | 10 |
| (2) | 5 | 5 | 5 | 5 | 2.5 | 5 | 5 | 10 |
| (3) | 10 | 5 | 5 | 5 | 10 | 10 | 10 | 5 |
| (4) | 2.5 | 1 | 2.5 | 2.5 | 5 | 2.5 | 2.5 | 1 |
| (5) | 5 | 5 | 10 | 5 | 5 | 10 | 5 | 5 |
| (6) | 10 | 10 | 10 | 5 | 10 | 5 | 10 | 5 |
| (7) | 10 | 10 | 25 | 5 | 25 | 10 | 10 | 10 |
| (8) | 10 | 5 | 10 | 10 | 25 | 5 | 10 | 25 |
| (9) | 2.5 | 5 | 5 | 5 | 10 | 5 | 5 | 5 |
| (10) | 1 | 1 | 2.5 | 1 | 2.5 | 2.5 | 1 | 1 |
| (11) | 5 | 5 | 5 | 10 | 5 | 10 | 5 | 5 |
| (12) | 5 | 5 | 10 | 10 | 10 | 25 | 5 | 5 |
| (13) | 5 | 5 | 2.5 | 5 | 10 | 2.5 | 2.5 | 5 |
| (14) | 5 | 5 | 10 | 5 | 10 | 10 | 5 | 5 |
| (15) | 25 | 10 | 10 | 5 | 10 | 25 | 10 | 10 |
| Comparative agent No. | | | | | | | | |
| (16) | 100 | 100 | 100 | 100 | 100 | 100 | 100 | 100 |
| (17) | 100 | 100 | 200 | >200 | 200 | 100 | 100 | 100 |
| (18) | 100 | >200 | 100 | 100 | >200 | 200 | 100 | >200 |
| (19) | 10 | 25 | 5 | 10 | 25 | 10 | 25 | 10 |

Note: Agent No. (19) represents benzalconium chloride.

TEST EXAMPLE 2

(Confirmation of algaecidal activities against algae)

With respect to the polymers obtained in Examples 1 to 15 and the agents of Comparative Examples, a test of algaecidal activities was carried out. The types of algae used in the test, the method and results are shown below.

(1) Test algae

Chlorophyta *Chlorella Vulgaris*

Cyanophyta *Oscillatoria Chlorina*

(2) Test method

The above *Chlorella Vulgaris* and *Oscillatoria Chlorina* were inoculated to Detmer culture media and incubated in an artificial incubator at 25° C. to obtain test solutions. Then, to a 1/3 diluted solution of Detmer culture medium (1.0 g of $Ca(NO_3)_2$, 0.25 g of KCl, 0.25 g of $MgSO_4 \cdot 7H_2O$, 0.25 g of $KH_2PO_4$ and 0.002 g of $FeCl_3$ in 3 l of $H_2O$), the agent solution and the test solution were added to predetermined concentrations, and the mixture was incubated in an artificial incubator at 25° C. During the incubation, stirring was continued by a stirrer. 48 hours later, the discoloration state of the algae was inspected, and the effective lowest concentration was taken as the minimum algaecidal concentration.

(3) Test results

In Table 2, the minimum algaecidal concentrations of the respective agents are shown. As is evident from Table 2, the polymers obtained in Examples 1 to 15 all exhibited excellent algaecidal activities at very low concentrations.

TABLE 2

| No. | Minumum algaecidal concentration (μg/ml) | |
|---|---|---|
| | *Chlorella Vularis* | *Oscillatoria Chiorina* |
| Agent No. of Example | | |
| (1) | 5 | 10 |
| (2) | 5 | 5 |
| (3) | 5 | 2.5 |
| (4) | 1 | 1 |
| (5) | 2.5 | 2.5 |
| (6) | 5 | 2.5 |
| (7) | 2.5 | 5 |
| (8) | 5 | 5 |
| (9) | 5 | 2.5 |
| (10) | 1 | 1 |
| (11) | 10 | 10 |
| (12) | 5 | 5 |
| (13) | 2.5 | 5 |
| (14) | 2.5 | 5 |
| (15) | 10 | 10 |
| Comparative agent No. | | |
| (16) | 50 | >100 |
| (17) | 50 | 50 |
| (18) | >100 | 100 |
| (19) | 5 | 5 |

Note: Agent No. (19) represents benzalconium chloride.

EXAMPLE 3

(Microbicidal activities against bacteria and fungi on floor)

(1) With respect to the polymers obtained in Examples 2, 4, 9 and 10 and the agent of Comparative Example (agent No. (19)), the effects of the agents were evaluated from the changes in the number of cells on the floor after using the agents.

(2) Test method

The agent of the Example (agent No. (2), (4), (9) or (10)) or Comparative Example (agent No. (19)) was dissolved in water to prepare a 1% aqueous solution.

After completion of the operation at a food plant (for kneaded products), the floor was washed with water and then 10 ml (100 mg as the active ingredient) of the above 1% aqueous solution per 1 m² of the floor surface, was uniformly sprayed on the floor surface. Two hours and 12 hours after the spray treatment, a section of 10 cm² at a center portion of the area treated with the agent was wiped with dry heat sterilized gauze impregnated with a predetermined amount of sterilized water, and 1 ml of the squeezed liquid was cultured by means of the following culture medium, whereupon the number of cells was measured. The number of cells of bacteria and fungi (inclusive of yeast) growing per 10 cm² on the floor was calculated.

Bacteria: Incubated at 30° C. for two days using a culture medium for bacteria (Tryptic soy agar culture medium, manufactured by Nissui Seiyaku K.K.).

Fungi: Incubated at 30° C. for 4 days using a culture medium for mold (potato dextrose agar culture medium, manufactured by Nissui Seiyaku K.K.).

(3) Test results

The test results are shown in Table 3.

In each of the cases treated with the polymers obtained in Examples 2, 4, 9 and 10, it was confirmed that sterilization and hygienic control on the floor were good as compared with the case treated with Comparative Example (agent No. (19)) and as compared with the non-treated area.

TABLE 3

| No. | Two hours after treatment with the agent | | 12 hours after treatment with the agent | |
|---|---|---|---|---|
| | Number of bacterial cells (N/10 cm²) | Number of fungi cells (N/10 cm²) | Number of bacterial cells (N/10 cm²) | Number of fungi cells (N/10 cm²) |
| Agent No. of Example (2) | 65 | 20 | 120 | 30 |
| Agent No. of Example (4) | 5 | 0 | 10 | 0 |
| Agent No. of Example (9) | 45 | 7 | 90 | 15 |
| Agent No. of Example (10) | 3 | 0 | 8 | 2 |
| Agent No. of Comparative Example (19) | 250 | 60 | 1060 | 260 |
| Non-treated area | 11110 | 450 | 24000 | 680 |

We claim:

1. A polycationic microbicidal and algaecidal agent containing a microbicidally or algaecidally acceptable vehicle and, as an active ingredient, a microbicidal or algaecidal effective amount of a polymer comprising repeating units of the following formula

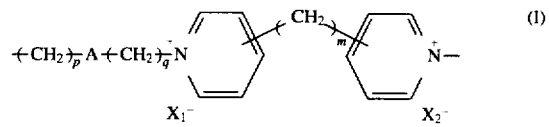

(wherein A is a single bond, an oxygen atom, a phenylene group, a dioxyethylene group or a tetramethyldisiloxane group, $X_1^-$ and $X_2^-$ may be the same or different and are counter anions in quaternary salts, p and q may be the same or different and are integers of from 1 to 6, and m is an integer of from 0 to 6, provided that A, $X_1^-$, $X_2^-$, p, q and m may be the same or optionally different for every repeating unit) and having a number average molecular weight of at least 1,000.

2. The microbicidal and algaecidal agent according to claim 1, wherein in the formula (I), the counter anions in quaternary salts represented by $X_1^-$ and $X_2^-$ are halogen ions, hydroxyl ions, carbonate ions, sulfate ions, hydrogen sulfate ions, sulfite ions, nitrate ions, phosphate ions, carboxylate ions, sulfonate ions or phosphonate ions.

3. The microbicidal and algaecidal agent according to claim 1, wherein in the formula (I), A is a phenylene group, both of p and q are 1, and m is 3.

4. The microbicidal and algaecidal agent according to claim 5, wherein the repeating units are represented by the formula:

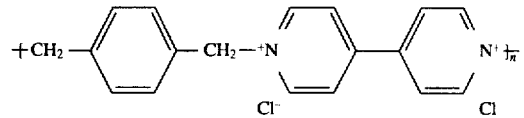

5. The microbicidal and algaecidal agent according to claim 1, wherein the repeating units are represented by the formula:

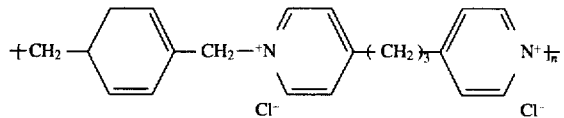

6. A method for inhibiting the growth of microbes or algae in a liquid or on a surface, comprising contacting the microbes or algae with a polymer comprising repeating units of the formula (I) as defined in claim 1 and having a number average molecular weight of at least 1,000.

* * * * *

UNITED STATES PATENT AND TRADEMARK OFFICE
CERTIFICATE OF CORRECTION

PATENT NO. : 5,616,317
DATED : April 1, 1997
INVENTOR(S) : Yu NAGASE, et al.

It is certified that error appears in the above-indentified patent and that said Letters Patent is hereby corrected as shown below:

On the title page, Item [30], the Foreign Application Priority Data is incorrect. It should read:

--[30]

Dec. 22, 1992  [JP]  Japan...........4-356485
    Dec. 22, 1992  [JP]  Japan...........4-356486. --

Signed and Sealed this

Twenty-sixth Day of August, 1997

Attest:

Attesting Officer

BRUCE LEHMAN

Commissioner of Patents and Trademarks